United States Patent [19]

Bru-Magniez et al.

[11] Patent Number: 5,229,505
[45] Date of Patent: Jul. 20, 1993

[54] N6-[3-(1-SUBSTITUTED)INDOLYLETHYL] ADENOSINE 5'-CARBOXAMIDES AND THEIR PHARMACEUTICAL COMPOSITIONS

[75] Inventors: Nicole Bru-Magniez, Paris; Timur Güngör, Rueil Malmaison; Jean-Marie Teulon, La Celle Saint Cloud, both of France

[73] Assignee: LABORATOIRES UPSA, Agen, France

[21] Appl. No.: 832,576

[22] Filed: Feb. 7, 1992

[30] Foreign Application Priority Data

Jan. 8, 1992 [FR] France ............... 92 00138

[51] Int. Cl.⁵ .......................... C07H 19/167
[52] U.S. Cl. ................. 536/27.62; 536/27.22
[58] Field of Search ............... 536/26; 514/46

[56] References Cited

U.S. PATENT DOCUMENTS 4,167,565  9/1979  Stein et al. ............... 514/46
5,023,244  6/1991  Goto et al. ............... 514/46

FOREIGN PATENT DOCUMENTS 0232813  8/1987  European Pat. Off. .
 267878  5/1988  European Pat. Off. .
2154527  5/1973  France .
8600310  1/1986  World Int. Prop. O. .
8803147  5/1988  World Int. Prop. O. .
8803148  5/1988  World Int. Prop. O. .
9205177  4/1992  World Int. Prop. O. .

OTHER PUBLICATIONS

Francis et al., "Highly Selective Adenosine A₂ Receptor Agonists in a Series of N-alkylated 2-Aminoadenosines," *J. Med. Chem.*, 34, 2570-2579 (1991).

Schillinger et al., "Metabolic Effects of N⁶-Substituted Adenosines in Rats," *Biochemical Pharmacology*, 23, 2283-2289 (1974).

Journal of Medicinal Chemistry, vol. 16, No. 4, Wash., US, pp. 358-364, Kiyomi Kikugawa et al.

*Primary Examiner*—Johnnie R. Brown
*Assistant Examiner*—L. Eric Crane
*Attorney, Agent, or Firm*—Dennison, Meserole, Pollack & Scheiner

[57] ABSTRACT

The present invention relates to the derivatives of the formula

Formula (I)

and their addition salts, and to their use in therapeutics, especially in the central nervous system as analgesics, anticonvulsants, antiepileptics, anxiolytics, antidepressants and neuroprotectors, and in the cardiovascular system as antiarrhythmics, antihypertensives and platelet aggregation inhibitors.

5 Claims, No Drawings

$N^6$-[3-(1-SUBSTITUTED)INDOLYLETHYL] ADENOSINE 5'-CARBOXAMIDES AND THEIR PHARMACEUTICAL COMPOSITIONS

The present invention relates, by way of novel products, to the adenosine derivatives of general formula (I) below and, if appropriate, their addition salts, in particular the pharmaceutically acceptable addition salts.

The compounds in question have a very valuable pharmacological profile insofar as they are active on the one hand in the central nervous system, where they possess especially analgesic properties but also anticonvulsant, antiepileptic, anxiolytic, antidepressant and neuroprotective properties, and on the other hand in the cardiovascular system, where they possess especially antiarrhythmic, antihypertensive and platelet aggregation inhibiting properties.

The present invention further relates to the method of preparing said products, to the synthesis intermediates and to the application of these products in therapeutics.

These adenosine derivatives have general formula (I):

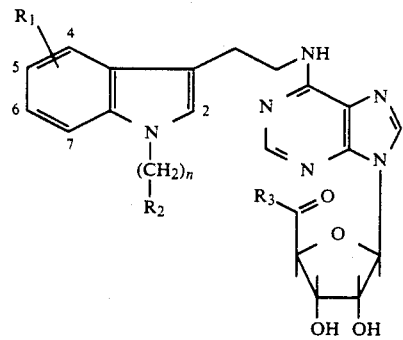

Formula (I)

in which:
$R_1$ can be a hydrogen atom, a halogen atom, a lower alkyl radical, a nitro radical or a trifluoromethyl radical and can be located in the 2, 4, 5, 6 or 7 position of the indole;
n is an integer from 0 to 4;
$R_2$ can be a lower alkyl radical, a $C_3$–$C_7$ cycloalkyl radical, a lower O-alkyl radical, a lower S-alkyl radical or a radical $COOR_4$, $R_4$ being a hydrogen atom or a lower alkyl radical; a phenyl or naphthyl radical which is unsubstituted or monosubstituted or polysubstituted by a halogen atom or a trifluoromethyl, nitro, hydroxyl, thio, lower alkyl, lower O-alkyl or lower S-alkyl group; a heteroaromatic group having from 5 to 7 atoms and containing 1 to 3 heteroatoms selected from nitrogen, oxygen and sulfur, which is unsubstituted or monosubstituted or polysubstituted by a halogen atom or a trifluoromethyl, nitro, hydroxyl, thio, lower alkyl, lower O-alkyl or lower S-alkyl group; or else, when n is equal to 2, 3 or 4, a group —$NR_5R_6$, $R_5$ and $R_6$ simultaneously being a lower alkyl radical or it being possible for $R_5$ and $R_6$ to form, together with the nitrogen atom to which they are attached, a ring of 5 to 7 atoms which can contain one to three heteroatoms selected from oxygen, sulfur or nitrogen; and
$R_3$ can be a group $OR_7$ or $NHR_7$, $R_7$ being a hydrogen atom, a lower alkyl radical, a $C_3$–$C_7$ cycloalkyl radical, a lower alkyl chain possessing an alcohol or thiol functional group, or else a group —$(CH_2)_n$—$NR_5R_6$, n, $R_5$ and $R_6$ being as defined above.

In the description and the claims, lower alkyl radical is understood as meaning a linear or branched hydrocarbon chain having from 1 to 6 carbon atoms. A lower alkyl radical is for example a methyl, ethyl, propyl, isopropyl, butyl, isobutyl, tert-butyl, pentyl, isopentyl, hexyl or isohexyl radical.

$C_3$–$C_7$ cycloalkyl radical is understood as meaning a saturated cyclic radical, preferably a cyclopropane, cyclobutane, cyclopentane, cyclohexane or cycloheptane radical.

Halogen is understood as meaning a chlorine, bromine, iodine or fluorine atom.

Lower alkyl chain possessing an alcohol or thiol functional group is understood as meaning a lower alkyl chain in which one of the hydrogen atoms has been substituted by a hydroxyl or thio group. Such a chain is for example the 1-hydroxy-2-methylpropan-2-yl chain.

Advantageously, the derivatives according to the invention are the derivatives of the aforementioned formula (I) in which:
$R_1$ is a hydrogen atom;
n is an integer equal to 0, 1 or 2;
$R_2$ is a lower alkyl radical, preferably methyl, a $C_3$–$C_7$ cycloalkyl radical, preferably cyclopentyl, or a lower O-alkyl radical, preferably methoxy; a phenyl radical which is unsubstituted or monosubstituted or polysubstituted by a halogen atom, preferably chlorine, or a lower alkyl group, preferably methyl; a naphthyl or pyridyl radical; or else, when n is equal to 2, a group —$NR_5R_6$, $R_5$ and $R_6$ simultaneously being a lower alkyl radical, preferably methyl, or it being possible for $R_5$ and $R_6$ to form, together with the nitrogen atom to which they are attached, a heterocycle selected from pyrrolidine, piperidine, piperazine and morpholine; and
$R_3$ is a group $NHR_7$, $R_7$ being a hydrogen atom, a lower alkyl radical, preferably ethyl, a $C_3$–$C_7$ cycloalkyl radical, preferably cyclopropyl, or a lower alkyl chain possessing an alcohol functional group.

According to one variant, $R_1$ is the hydrogen atom.
According to one variant, n is a number equal to 0.
According to another variant, n is a number equal to 1.
According to another variant, n is a number equal to 2.
According to one variant, $R_2$ is a parachlorophenyl
According to another variant, $R_2$ is a cyclopentane radical.
According to another variant, $R_2$ is an isopropyl radical.
According to another variant, $R_2$ is a 2,5-di-methylphenyl.
According to another variant, $R_2$ is a piperidine radical.
According to one variant, $R_3$ is an N-cyclopropylamine radical.

The particularly preferred compounds of the invention are selected from the derivatives of the formulae

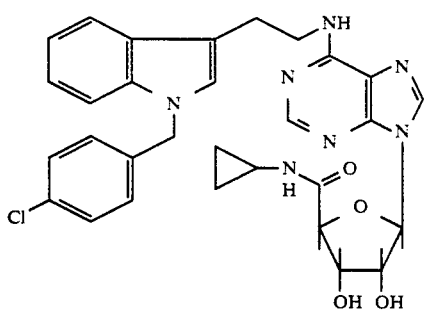

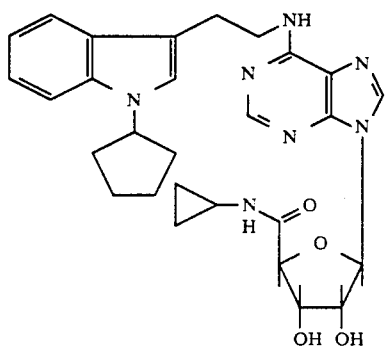

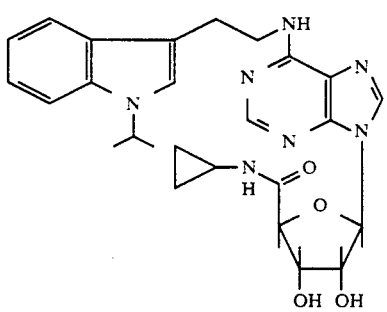

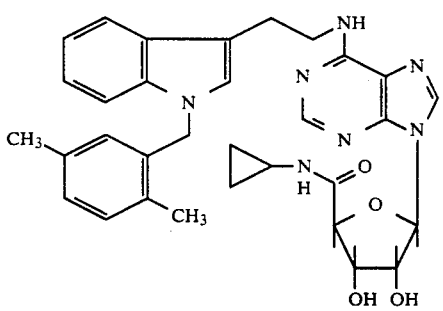

According to the invention, the compounds of formula (I) may be synthesized in the following manner:

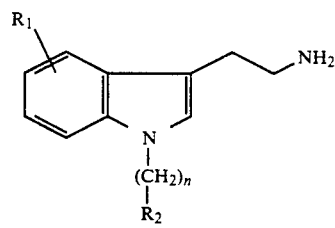

Formula (II)

in which $R_1$, $R_2$ and n are as defined above, with the 6-halogenopurine ribosides of formula (III):

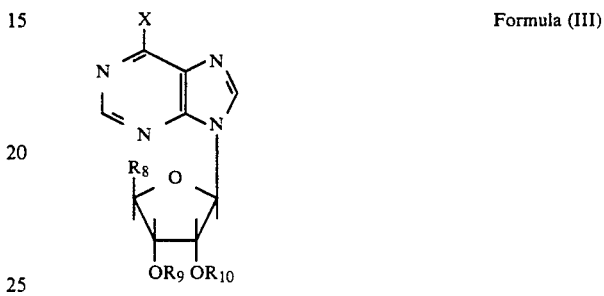

Formula (III)

in which X is a halogen atom, preferably chlorine or bromine, $R_8$ can be the group $COR_3$, $r_3$ being as defined above, or the $CH_2OH$ group, and $R_9$ and $R_{10}$ are protecting groups for the alcohol functional group, such as, for example, an acetyl, a benzoyl or a benzyl, or can together form another protecting group, for example of the dioxolan structure, in a solvent such as, for example, an alcohol or an aprotic solvent such as dimethylformamide, in the presence of a base such as triethylamine, pyridine or sodium, potassium or calcium carbonate, or else in the presence of two equivalents of the amine of formula (II), at a temperature of between 20° and 140° C., will give the compounds of formula (IV):

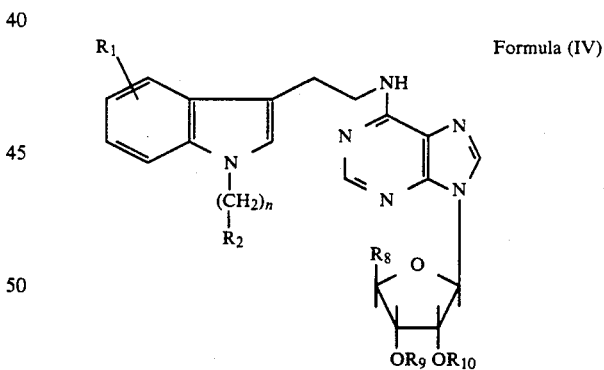

Formula (IV)

in which $R_1$, $R_2$, $R_8$, $R_9$, $R_{10}$ and n are as defined above. In the case where the radical $R_8$ is the $CH_2OH$ group, it will be possible to oxidize it with chromium trioxide in accordance with the method described by: R. R. SCHMIDT and H. J. FRITZ, Chem. Ber. 1970, 103, 1867, or with potassium permanganate in the presence of aqueous ammonia according to: P. J. HARPER and A. HAMPTON, J. Org. Chem. 1970, 35, no. 5, 1688.

The resulting ribouronic acid will then be converted to the acid chloride by reaction with thionyl chloride, for example, and then to an amide by reaction with an amine in accordance with the methods known to those skilled in the art; deprotection of the secondary alcohols $OR_9$ and $OR_{10}$ may be carried out in accordance with different methods, namely in a basic medium such as ammoniacal alcohol, or in an acid medium such as a normal hydrochloric acid solution or a formic acid solution, at temperatures varying from 0° to 70° C. depending on the nature of the protecting groups.

These reaction sequences make it possible to convert the derivatives of formula (IV) to derivatives of formula (I).

The compounds of formula (II) may be obtained:
either by the direct alkylation of indolethylamine derivatives of formula (V):

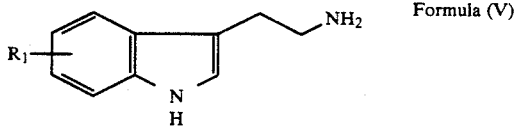

Formula (V)

in which $R_1$ is as defined above, which are commercially available or whose synthesis is described in the literature: P. L. JULIAN, E. W. MEYER and H. C. PRINTY, Heterocyclic Compounds, John Wiley and Sons, Inc. New York, 1952, vol. 3, chapter 1, p. 51-57, and J. HARLEY-MASON and A. H. JACKSON, J. Chem. Soc. 1954, 1165, with derivatives of formula (VI):

Formula (VI)

in which $R_2$ and n are as defined above, Y being a halogen atom, preferably chlorine or bromine, in the presence of a metalating agent such as sodium or lithium hydride, or of a sodium or potassium alcoholate, in an organic solvent such as an alcohol or such as dimethylformamide or N-methylpyrrolidone, at temperatures of between 0° and 60° C.;

or by the alkylation of a 3-formylindole of formula (VII):

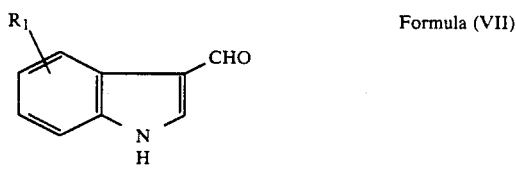

Formula (VII)

in which $R_1$ is as defined above, with derivatives of formula (VI), in the presence of a metalating agent such as sodium or lithium hydride, or of a sodium or potassium alcoholate or sodium or potassium carbonate, in an organic solvent such as an alcohol or dimethylformamide, to give the derivatives of formula (VIII):

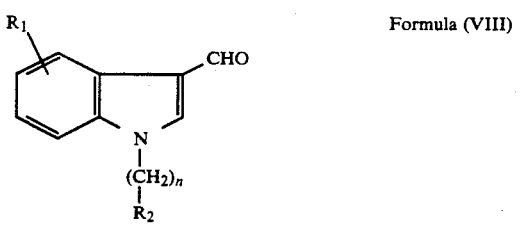

Formula (VIII)

in which $R_1$, $R_2$ and n are as defined above.

These derivatives are then reacted with nitromethane, in the presence of ammonium acetate, to give the nitrovinylindoles of formula (IX):

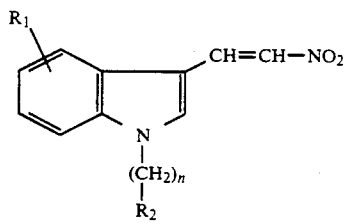

Formula (IX)

in which $R_1$, $R_2$ and n are as defined above.

These derivatives will be reduced by catalytic hydrogenation in the presence of Raney nickel, or with lithium aluminum hydride, to give compounds of formula (II).

Other methods of synthesizing indolethylamine derivatives are generally described in the literature and can be used. An example which may be mentioned is the method of synthesis which consists in reacting oxalyl chloride with the appropriate indole according to the following reference: M. E. SPEETER and W. C. ANTHONY, J. Am. Chem. Soc. 1954, 76, 6208, and then amidating the product and reducing the amide functional group with lithium aluminum hydride.

The 3-formylindoles of formula (VII) used in these syntheses are commercially available or are known to those skilled in the art: Organic syntheses Coll. vol. IV, 539, or can be obtained by methods described in the literature: Organic Syntheses Coll. Vol. IV, 542, references cited.

The 6-halogenopurines of formula (III) are prepared from inosine in accordance with methods described in the literature: R. R. SCHMIDT and H. J. FRITZ, Chem Ber. 1970, 103, 1867, H. M. KISSMAN and M. J. WEISS, J. Org. Chem. 1956, 21, 1053, B. R. BAKER, K. HEWSON, H. J. THOMAS and J. A. JOHNSON JR, J. Org. Chem. 1957, 22, 954, and J. ZEMLICKA and F. SORM, *Coll. Czech. Chem. Commun.* 1965, 30, (6), 1880.

The compounds of formula (I) as defined above, and their addition salts, in particular the pharmaceutically acceptable addition salts, possess a good affinity for adenosine receptors. This affinity gives them a good activity in the central nervous system with especially analgesic properties but also anxiolytic, antidepressant and neuroprotective properties, and in the cardiovascular system with antiarrhythmic, antihypertensive and platelet aggregation inhibiting properties.

Adenosine and adenosine analogs have antinociceptives effects after systemic administration: H. D. VAPAATALO et al., Arzneimittelforsch. 1975, 25, 407, and M. T. HOLMGREN et al., J. Pharm Pharmacol. 1983, 35, 679, and after central administration: G. G. YARBOROUGH et al., Eur. J. Pharmacol. 1971, 76, 137, and G. E. DELANDER et al., Eur. J. Pharmacol. 1987, 139, 215.

This action is probably mediated via the adenosine receptors in the spine (cf. YARBOROUGH and DELANDER, references cited above).

These properties justify the application of the derivatives of formula (I) in therapeutics and the invention further relates, by way of drugs, to the products as defined by formula (I) above, and their addition salts, in particular pharmaceutically acceptable addition salts.

Thus the invention also covers a pharmaceutical composition which comprises a pharmaceutically effective amount of at least one compound of formula (I) as defined above, or one of its pharmaceutically acceptable addition salts, which may or may not be incorporated in a pharmaceutically acceptable excipient, vehicle or carrier.

These compositions can be administered by the buccal, rectal, parenteral, transdermal or ocular route.

These compositions can be solid or liquid and can be in the pharmaceutical forms commonly used in human medicine, such as, for example, simple or coated tablets, gelatin capsules, granules, suppositories, injectable preparations, transdermal systems and eye lotions. They are prepared by the customary methods. The active principle, which consists of a pharmaceutically effective amount of at least one compound of formula (I) as defined above, or one of its pharmaceutically acceptable addition salts, can be incorporated therein with excipients normally employed in these pharmaceutical compositions, such as talc, gum arabic, lactose, starch, magnesium stearate, polyvidone, cellulose derivatives, cacao butter, semisynthetic glycerides, aqueous or non-aqueous vehicles, fatty substances of animal or vegetable origin, glycols, various wetting agents, dispersants or emulsifiers, silicone gels, certain polymers or copolymers, preservatives, flavorings and colors.

The invention also covers a pharmaceutical composition with analgesic, anxiolytic, antidepressant and neuroprotective activity affording especially a favorable treatment for pain and anxiety, which comprises a pharmaceutically effective amount of at least one compound of formula (I) given above, or one of its pharmaceutically acceptable addition salts, which may or may not be incorporated in a pharmaceutically acceptable excipient, vehicle or carrier.

The invention also covers a pharmaceutical composition with cardiovascular activity affording a favorable treatment for arrhythmia and hypertension and possessing platelet aggregation inhibiting properties, which comprises a pharmaceutically effective amount of at least one compound of formula (I) given above, or one of its pharmaceutically acceptable addition salts, which may or may not be incorporated in a pharmaceutically acceptable excipient, vehicle or carrier.

The invention also covers a method of preparing a pharmaceutical composition, which comprises incorporating a pharmaceutically effective amount of at least one compound of formula (I) as defined above, or one of its pharmaceutically acceptable addition salts, into a pharmaceutically acceptable excipient, vehicle or carrier. According to one embodiment, a pharmaceutical composition with analgesic and anxiolytic activity is prepared which affords especially a favorable treatment for pain and anxiety, and according to another embodiment, a pharmaceutical composition with cardiovascular activity is prepared which affords especially a favorable treatment for arrhythmia and hypertension.

According to another variant, a pharmaceutical composition is formulated as gelatin capsules of tablets containing from 5 to 300 mg of active ingredient, or as injectable preparations containing from 0.1 mg to 100 mg of active ingredient. Formulations as suppositories, ointments, creams, gels or aerosol preparations may also be used.

The invention also covers a method of therapeutic treatment for mammals, which comprises administering to this mammal a therapeutically effective amount of at least one compound of formula (I) as defined above, or one of its pharmaceutically acceptable addition salts. According to one variant of this method of treatment, the compound of formula (I), either by itself or in association with a pharmaceutically acceptable excipient, is formulated as gelatin capsules or tablets containing from 5 mg to 300 mg of active ingredient for oral administration, or as injectable preparations containing from 0.1 to 100 mg of active ingredient, or else as suppositories, ointments, creams, gels or aerosol preparations.

In human and animal therapeutics, the compounds of formula (I) and their salts can be administered by themselves or in association with a physiologically acceptable excipient, in any form, in particular in the form of gelatin capsules or tablets for oral administration or in the form of an injectable solution for parenteral administration. Other forms of administration, such as suppositories, ointments, creams, gels or aerosol preparations, can be envisaged.

As will be clearly apparent from the pharmacological tests given at the end of the description, the compounds according to the invention can be administered in human therapeutics for the afore-mentioned indications, orally in the form of tablets or gelatin capsules containing from 5 mg to 300 mg of active ingredient, or parenterally in the form of injectable preparations containing from 0.1 mg to 100 mg of active ingredient, in one or more daily administrations for an adult with an average weight of 60 to 70 kg.

In animal therapeutics, the daily dose which can be used should normally be between 0.1 and 50 mg per kg by oral administration and between 0.01 and 1 mg per kg by intravenous administration.

Further characteristics and advantages of the invention will be understood more clearly from the following description of some examples, which in no way imply a limitation but are given by way of illustration.

EXAMPLE 1

β-D-Ribofuranuronamido-1-(6-chloro-9H-purin-9-yl)-N-cyclopropyl-1-deoxy-2,3-O-(1-methylethylidene)

Formula (III): X=Cl, $R_s$:

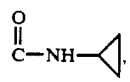

$R_9, R_{10}$: isopropylidene 20 g of 2',3'-O-isopropylidene-6-chloropurine-5'-uronic acid, prepared according to SCHMIDT R. R. and FRITZ H. J., Chem Ber. 1970, 103)(6), 1867-71, in 500 ml of anhydrous $CHCl_3$ stabilized with amylene, are refluxed for 5 h in the presence of 86 ml of $SOCl_2$ and 10 ml of anhydrous DMF.

The excess $SOCl_2$ and the solvents are distilled. The residue is taken up with 200 ml of anhydrous chloroform and added dropwise, under nitrogen, to a mixture of 150 ml of $CHCl_3$ and 41 ml of cyclopropylamine, cooled to 5° C. beforehand. The temperature of the reaction mixture is kept below 10° C. during the addition of the acid chloride.

The mixture is left to react for a further 30 min and then washed 3 times with a dilute HCl solution and then with a sodium bicarbonate solution. A final washing with water, followed by drying and evaporation of the solvent, gives 26.3 g of a brown oil.

Purification by chromatography on silica gel (eluent: $CH_2Cl_2$ 90%/acetone 10%) gives 15.7 g of β-D-ribofuranuronamido-1-(6-chloro-9H-purin-9-yl)-N- cyclopropyl-1-deoxy-2,3-O-(1-methylethylidene) in the form of an amorphous solid.

The compounds of Examples 2 to 4 were prepared by the procedure of Example 1 using the appropriate amines:

EXAMPLE 2

β-D-Ribofuranuronamido-1-(6-chloro-9H-purin-9-yl)-N-cyclopropyl-1-deoxy-N-ethyl-2,3-O-(1-methylethylidene)

Formula (III): X=Cl, R$_8$:

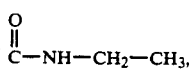

R$_9$,R$_{10}$: isopropylidene

A yellowish oil purified by chromatography on silica gel (eluent: chloroform 95%/methanol 5%) to give a solid melting at 91° C.

EXAMPLE 3

β-D-Ribofuranuronamido-1-(6-chloro-9H-purin-9-yl)-N-cyclopropyl-1-deoxy-N-(1-hydroxy-2-methylpropan-2-yl)-2,3-O-(1-methylidene)

Formula (III): X=Cl, R$_8$:

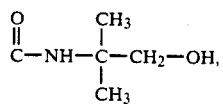

R$_9$,R$_{10}$: isopropylene

A brown oil purified by chromatography on silica gel (eluent: chloroform 90%/methanol 10%).

EXAMPLE 4

β-D-Ribofuranuronamido-1-(6-chloro-9H-purin-9-yl)-N-cyclopropyl-1-deoxy-N-isopropyl-2,3-O-(1-methylethylidene)

Formula (III): X=Cl, R$_8$:

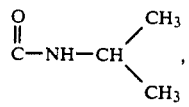

R$_9$,R$_{10}$: isopropylidene

An orange oil purified by chromatography on silica gel (eluent: CHCl$_3$ 90%/acetone 10%).

EXAMPLE 5

1-(4-Chlorobenzyl)-3-formylindole

Formula (VIII): R$_1$=H, n=1, R$_2$=4-chlorophenyl

A solution of 58 g of 3-formylindole, 55.9 g of K$_2$CO$_3$ and 70.9 g of p-chlorobenzyl chloride in 200 ml of DMF is refluxed for 2 h. After cooling, the mixture is poured into 2 l of water and triturated. The precipitate obtained is filtered off, washed with water and then taken up with isopropanol, filtered off, compressed and washed with pentane to give 120 g of a cream-colored solid.

Purification by recrystallization from ethanol gives 84.4 g of 1-(4-chlorobenzyl)-3-formylindole melting at 122° C.

The following compounds of Examples 6 to 16 were prepared by the method of Example 5:

EXAMPLE 6

1-Benzyl-3-formylindole

Formula (VIII): R$_1$=H, n=1, R$_2$=phenyl
Recrystallization from ethanol.
Melting point: 111° C. (literature: 113°–114° C.—A. KALIR and S. Szara, J. Med. Chem. (1966), vol. 9, p. 793).

EXAMPLE 7

1-(2,6-Dichlorobenzyl)-3-formylindole

Formula (VIII): R$_1$=H, N=1, R$_2$=2,6-dichlorphenyl
Recrystallization from 2-methoxyethanol.
Melting point: 160° C.

EXAMPLE 8

1-(Naphth-1-ylmethyl)-3-dormylindole

Formula (VIII): R$_1$=H, n=1, R$_2$=naphthyl
A crude solid used as such in the next step.

EXAMPLE 9

3-Formyl-1-(pyrid-3-yl)indole

Formula (VIII): R$_1$=H, n=1, R$_2$=pyrid-3-yl
Purification by chromatography on silica gel (eluent: CHCl$_3$ 95%/methanol 5%).
Melting point: 88° C.

EXAMPLE 10

1-(4-Methylbenzyl)-3-formylindole

Formula (VIII): R$_1$=H, n=1, R$_2$=4-methylphenyl
A crude solid used as such in the next step.
Melting point: 118° C.

EXAMPLE 11

1-(3,4-Dimethylbenzyl)-3-formylindole

Formula (VIII): R$_1$=H, n=1, R$_2$=3,4-dimethylphenyl
A brown oil used as such in the next step.

EXAMPLE 12

1-(2,5-Dimethylbenzyl)-3-formylindole

Formula (VIII): R$_1$=H, n=1, R$_2$=2,5-dimethylphenyl
A crude solid used as such in the next step.
Melting point: 139° C.

EXAMPLE 13

1-(2-Methoxyethyl)-3-formylindole

Formula (VIII): R$_1$=H, n=2, R$_2$=methoxy
A brown oil used as such in the next step.

EXAMPLE 14

1-Cyclopentyl-3-formylindole

Formula (VIII): R$_1$=H, n=0, R$_2$=cyclopentyl
A brown oil purified by chromatography on silica gel (eluent: chloroform 90%/methanol 10%).

EXAMPLE 15

3-Formyl-1-isopropylindole

Formula (VIII): R$_1$=H, n=0, R$_2$=isopropyl
A brown oil used as such in the next step.

EXAMPLE 16

3-Formyl-1-(2-morpholinoethyl)-3-formylindole

Formula (VIII): $R_1=H$, $n=2$, $R_2=$morpholino
A solid used as such in the next step.
Melting point: 80° C.

EXAMPLE 17

1-(4-Chlorobenzyl)-3-(2-nitrovinyl)indole

Formula (IX): $R_1=H$, $n=1$, $R_2=$4-chlorophenyl
80.9 g of 1-(4-chlorobenzyl)-3-formylindole, prepared in Example 5, 18 g of ammonium acetate and 300 ml of nitromethane are refluxed for 30 min.

An orange precipitate appears after cooling. It is filtered off and washed with water and then with isopropanol and hexane to give 81.1 g of orange crystals of 1-(4-chlorobenzyl)-3-(2-nitrovinyl)indole.
Melting point: 178° C.

The nitrovinylindoles of Examples 18 to 28 were prepared by the procedure of Example 17:

EXAMPLE 18

1-Benzyl-3-(2-nitrovinyl)indole

Formula (IX): $R_1=H$, $n=1$, $R_2=$phenyl
Melting point: 130° C.

EXAMPLE 19

1-(2,6-Dichlorobenzyl)-3-(2-nitrovinyl)-indole

Formula (IX): $R_1=H$, $n=1$, $R_2=$2,6-dichlorophenyl
Melting point: 170° C.

EXAMPLE 20

1-Naphthylmethyl-3-(2-nitrovinyl)indole

Formula (IX): $R_1=H$, $n=1$, $R_2=$naphthyl
Melting point: 196° C.

EXAMPLE 21

1-(Pyrid-3-ylmethyl)-3-(2-nitrovinyl)indole

Formula (IX): $R_1=H$, $n=1$, $R_2=$pyrid-3-yl
Melting point: 165°-170° C.

EXAMPLE 22

1-(4-Methylbenzyl)-3-(2-nitrovinyl)indole

Formula (IX): $R_1=H$, $n=1$, $R_2=$4-methylphenyl
An orange oil purified by chromatography on silica gel (eluent: chloroform 95%/isopropylamine 5%).

EXAMPLE 23

1-(3,4-Dimethylbenzyl)-3-(2-nitrovinyl)indole

Formula (IX): $R_1=H$, $n=1$, $R_2=$3,4-dimethylphenyl
Melting Point: 135° C.

EXAMPLE 24

1-(2,5-Dimethylbenzyl)-3-(2-nitrovinyl)indole

Formula (IX): $R_1=H$, $n=1$, $R_2=$2,5-dimethylphenyl
Melting point: 145° C.

EXAMPLE 25

1-(2-Methoxyethyl)-3-(2-nitrovinyl)indole

Formula (IX): $R_1=H$, $n=2$, $R_2=$methoxy
Melting point: 132° C.

EXAMPLE 26

1-Cyclopentyl-3-(2-nitrovinyl)indole

Formula (IX): $R_1=H$, $n=0$, $R_2=$cyclopentyl
An orange oil purified by chromatography on silica gel. Eluent: methylene chloride.

EXAMPLE 27

1-Isopropyl-3-(2-nitrovinyl)indole

Formula (IX): $R_1=H$, $n=0$, $R_2=$isopropyl
An orange oil used as such in the next step.

EXAMPLE 28

1-(2-Morpholinoethyl)-3-(2-nitrovinyl)indole

Formula (IX): $R_1=H$, $n=2$, $R_2=$morpholino
Melting point: 114° C.

EXAMPLE 29

1-(4-Chlorobenzyl)-3-(2-aminoethyl)indole

Formula (II): $R_1=H$, $n=1$, $R_2=$4-chlorophenyl
52.5 G of LiAlH$_4$ are added in small portions to 500 ml of anhydrous THF. The temperature is left to rise to 50° C. Without cooling this solution, a solution of 78.2 g of 1-(4-chlorobenzyl)-3-(2-nitrovinyl)indole, prepared in Example 17, in 1000 ml of anhydrous THF is added dropwise.

The mixture is refluxed for 1 h 30 min and cooled. A saturated aqueous solution of Na$_2$SO$_4$ is added dropwise and the mixture is filtered on Cèlite 545. After decantation, the organic phase is concentrated to give an orange oil.

The compound is purified firstly by distillation (boiling point: 180°-188° C. under 0.1 mm of mercury) and then by recrystallization of the hydrochloride from ethanol to give 38.1 g of 1-(4-chlorobenzyl)-3-(2-aminoethyl)indole hydrochloride.
Melting point of the base: 87° C.
Melting point of the hydrochloride: 212° C.

EXAMPLE 30

1-(4-Chlorobenzyl)-3-(2-aminoethyl)indole

Formula (II): $R_1=H$, $n=1$, $R_2=$4-chlorophenyl
10 g of 3-aminoethylindole are dissolved in 50 cm$^3$ of DMF. 5.6 g of NaH (60%) are then added.

The mixture is stirred for 30 min at room temperature.

A solution of 11.2 g of p-chlorobenzyl chloride in 10 ml of DMF is added dropwise. The mixture is heated at 55° C. for 2 h and cooled. The insoluble material is filtered off. The filtrate is concentrated under vacuum and the residue is taken up with methylene chloride and washed with water. After drying, the organic phase is concentrated to give 20.4 g of a brown oil.

Purification by chromatography on silica gel (eluent: CHCl$_3$ 95%/isopropylamine 5%) gives 9.7 g of 1-(chlorobenzyl)-3-(2-aminoethyl)indole.
Melting point of the hydrochloride: 214° C.

The following compounds of Examples 31 to 45 were prepared by one of the procedures of Examples 29 or 30:

EXAMPLE 31

1-Benzyl-3-(2-aminoethyl)indole

Formula (II): $R_1=H$, $n=1$, $R_2=$phenyl

The hydrochloride purified by recrystallization from isopropanol.
Melting point: 176°-178° C.

EXAMPLE 32

1-(2,6-Dichlorobenzyl)-3-(2-aminoethyl)indole

Formula (II): $R_1=H$, $n=1$, $R_2=2,6$-dichlorophenyl
Melting point: 68° C.

EXAMPLE 33

1-Naphthylmethyl-3-(2-aminoethyl)indole

Formula (II): $R_1=H$, $n=1$, $R_2=$naphthyl
An orange oil purified by chromatography on silica gel (eluent: chloroform 95%/isopropylamine 5%).

EXAMPLE 34

1-(Pyrid-3-ylmethyl)-3-(2-aminoethyl)indole

Formula (II): $R_1=H$, $n=1$, $R_2=$pyrid-3-yl
An oil purified by chromatography on silica gel (eluent: chloroform 95%/isopropylamine 5%).

EXAMPLE 35

1-(4-Methylbenzyl)-3-(2-aminoethyl)indole

Formula (II): $R_1=H$, $n=1$, $R_2=4$-methylphenyl
An orange oil purified by chromatography on silica gel (eluent: chloroform 95%/isopropylamine 5%).

EXAMPLE 36

1-(3,4-Dimethylbenzyl)-3-(2-aminoethyl)indole

Formula (II): $R_1=H$, $n=1$, $R_2=3,4$-dimethylphenyl
A colorless oil purified by chromatography on silica gel (eluent: methylene chloride 95%/isopropylamine 5%).

EXAMPLE 37

1-(2,5-Dimethylbenzyl)-3-(2-aminoethyl)indole

Formula (II): $R_1=H$, $n=1$, $R_2=2,5$-dimethylphenyl
An orange oil purified by chromatography on silica gel (eluent: methylene chloride 95%/isopropylamine 5%).

EXAMPLE 38

1-(2-Methoxyethyl)-3-(2-aminoethyl)indole

Formula (II): $R_1=H$, $n=1$, $R_2=$methoxy
An orange oil purified by chromatography on silica gel (eluent: chloroform 90%/isopropylamine 10%).

EXAMPLE 39

1-Cyclopentyl-3-(2-aminoethyl)indole

Formula (II): $R_1=H$, $n=0$, $R_2=$cyclopentyl
A yellowish oil purified by chromatography on silica gel (eluent: chloroform 95%/isopropylamine 5%).

EXAMPLE 40

1-Isopropyl-3-(2-aminoethyl)indole

Formula (II): $R_1=H$, $n=0$, $R_2=$isopropyl
An orange oil purified by chromatography on silica gel (eluent: chloroform 95%/isopropylamine 5%).

EXAMPLE 41

1-(2-N,N-Dimethylaminoethyl)-3-(2-aminoethyl)indole

Formula (II): $R_1=H$, $n=2$, $R_2=$N,N-dimethylamino
An orange oil purified by chromatography on silica gel (eluent: chloroform 95%/isopropylamine 5%).

EXAMPLE 42

1-(2-Morpholinoethyl)-3-(2-aminoethyl)indole

Formula (II): $R_1=H$, $n=2$, $R_2=$morpholino
An orange oil purified by chromatography on silica gel (eluent: chloroform 95%/isopropylamine 5%).

EXAMPLE 43

1-(2-Piperidinoethyl)-3-(2-aminoethyl)indole formula (II): $R_1=H$, $n=2$, $R_2=$piperidino
An orange oil purified by chromatography on silica gel (eluent: methylene chloride 95%/isopropylamine 5%).

EXAMPLE 44

1-Pyrrolidinoethyl-3-(2-aminoethyl)indole

Formula (II): $R_1=H$, $n=2$, $R_2=$pyrrolidino
An orange oil purified by chromatography on silica gel (eluent: methylene chloride 95%/isopropylamine 5%).

EXAMPLE 45

1-(3,4-Dichlorobenzyl)-3-(2-aminoethyl)indole

Formula (II): $R_1=H$, $n=1$, $R_2=3,4$-dichlorophenyl
Melting point: 196° C.

EXAMPLE 46

β-D-Ribofuranuronamido-1-[6-[[2-[1-(4-chlorobenzyl)indol-3-yl]ethyl]amino]-9H-purin-9-yl]-N-cyclopropyl-1-deoxy-2,3-O-(1-methylethylidene)

Formula (IV): $R_1=H$, $n=1$, $R_2=4$-chlorophenyl, $R_8=$

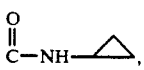

$R_9, R_{10}=$

Under a stream of nitrogen, 49 g of 1-(4-chlorobenzyl)-3-(2-aminoethyl)indole hydrochloride, prepared by one of the procedures of Examples 29 or 30, are suspended in 100 ml of ethanol. The suspension is neutralized with 5.1 ml of triethylamine, and 4.1 g of β-D-ribofuranuronamido-1-(6-chloro-9H-purin-9-yl)-N-cyclopropyl-1-deoxy-2,3-O-(1-methylethylidene), prepared in Example 1, are then added.

The whole is refluxed for 7 h and left to stand overnight. The solvent is evaporated off and the residue is taken up with chloroform, washed with water, dried and concentrated. The solid obtained is chromatographed on silica gel (eluent: chloroform 90%/methanol 10%) to give 7.2 g of an amorphous solid.

The derivatives of Examples 47 to 59 were prepared in the form of amorphous solids by the procedure of Example 46 using the uronamide of Example 1:

EXAMPLE 47

β-D-Ribofuranuronamido-N-cyclopropyl-1-deoxy-1-[6-[[2-[1-(methoxyethyl)indol-3-yl]ethyl]amino]-9H-purin-9-yl]-2,3-O-(1-methylethylidene)

Formula (IV): $R_1$=H, n=2, $R_2$=methoxy, $R_8$=

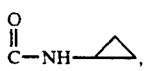

$R_9,R_{10}$=

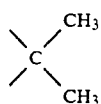

EXAMPLE 48

η-D-Ribofuranuronamido-1-[6-[[2-[1-cyclopentylindol-3-yl]ethyl]amino]-9H-purin-9-yl]-N-cyclopropyl-1-deoxy-2,3-O-(1-methylethylidene)

Formula (IV): $R_1$=H, n=0, $R_2$=cyclopentyl, $R_8$=

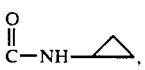

$R_9,R_{10}$=

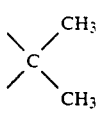

EXAMPLE 49

β-D-Ribofuranuronamido-N-cyclopropyl-1-deoxy-1-[6-[[2-[1-isopropylindol-3-yl]ethyl]amino]-9H-purin-9-yl]-2,3-O-(1-methylethylidene)

Formula (IV): $R_1$=H, n=0, $R_2$=isopropyl, $R_8$=

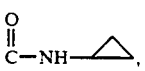

$R_9,r_{10}$=

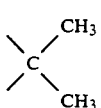

EXAMPLE 50

β-D-Ribofuranuronamido-N-cyclopropyl-1-deoxy-1-[6-[[2-[1-(4-methylbenzyl)indol-3-yl]ethyl]amino]-9H-purin-9-yl]-2,3-O-(1-methylethylidene)

Formula (IV): $R_1$=H, n=1, $R_2$=4-methylphenyl, $R_8$=

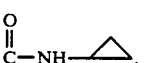

$R_9,R_{10}$=

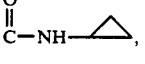

EXAMPLE 51

β-D-Ribofuranuronamido-N-cyclopropyl-1-deoxy-1-deoxy-1-[6-[[2-[1-(3,4-dimethylbenzyl)indol-3-yl]ethyl]amino]-9H-purin-9-yl]-2,3-O-(1-methylethylidene)

Formula (IV): $R_1$=H, n=1, $R_2$=3,4-dimethylphenyl, $R_8$=

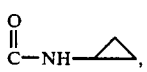

$R_9,R_{10}$=

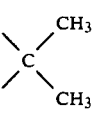

EXAMPLE 52

β-D-Ribofuranuronamido-N-cyclopropyl-1-deoxy-1-[6-[[2-1-(2,5-dimethylbenzyl)indol-3-yl]ethyl]amino]-9H-purin-9-yl]-2,3-O-(1-methylethylidene)

Formula (IV): $R_1$=H, n=1, $R_2$=2,5-dimethylphenyl, $R_8$=

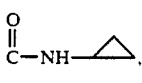

$R_9,R_{10}$=

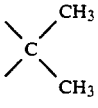

EXAMPLE 53

β-D-Ribofuranuronamido-N-cyclopropyl-1-deoxy-1-[6-[[2-[1-(2-N-morpholinoethyl)indol-3-yl]ethyl]amino]-9H-purin-9-yl]-2,3-O-(1-methylethylidene)

Formula (IV): $R_1$=H, n=2, $R_2$=morpholino, $R_8$=

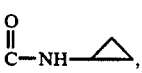

$R_9,R_{10}$=

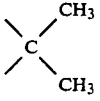

EXAMPLE 54

β-D-Ribofuranuronamido-N-cyclopropyl-1-deoxy-1-[6-[[2-[1-(2-N,N-dimethylaminoethyl)indol-3-yl]ethyl]amino]-9H-purin-9-yl]-2,3-O-(1-methylethylidene)

Formula (IV): $R_1$=H, n=2, $R_2$=N,N-dimethylamino, $R_8$=

$R_9, R_{10}$=

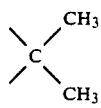

EXAMPLE 55

β-D-Ribofuranuronamido-N-cyclopropyl-1-deoxy-2,3-O-(1-methylethylidene)-1-[6-[[2-[1-(2-N-piperidinoethyl)indol-3-yl]ethyl]amino]-9H-purin-9-yl]

Formula (IV): $R_1$=H, n=2, $R_2$=piperidino, $R_8$=

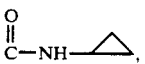

$R_9, R_{10}$=

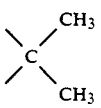

EXAMPLE 56

β-D-Ribofuranuronamido-N-cyclopropyl-1-deoxy-2,3-O-(1-methylethylidene)-1-[6-[[2-[1-(2-N-piperidinoethyl)indol-3-yl]ethyl]amino]-9H-purin-9-yl]

Formula (IV): $R_1$=H, n=2, $R_2$=pyrrolidino, $R_8$=

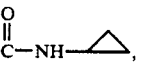

$R_9, R_{10}$=

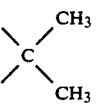

EXAMPLE 57

β-D-Ribofuranuronamido-N-cyclopropyl-1-deoxy-2,3-O-(1-methylethylidene)-1-[6-[[2-[1-(3,4-dichlorobenzyl)indol-3-yl]ethyl]amino]-9H-purin-9-yl]-2,3-O-(1-methylethylidene)

Formula (IV): $R_1$=H, n=1, $R_2$=3,4-dichlorophenyl, $R_8$=

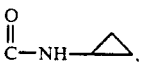

$R_9, R_{10}$=

EXAMPLE 58

β-D-Ribofuranuronamido-N-cyclopropyl-1-deoxy-2,3-O-(1-methylethylidene)-1-[6-[[2-[1-(pyrid-3-ylmethyl)indol-3-yl]ethyl]amino]-9H-purin-9-yl]

Formula (IV): $R_1$=H, n=1, $R_2$=pyrid-3-yl, $R_8$=

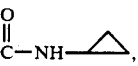

$R_9, R_{10}$=

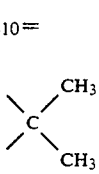

EXAMPLE 59

β-D-Ribofuranuronamido-N-cyclopropyl-1-deoxy-2,3-O-(1-methylethylidene)-1-[6-[[2-[1-(naphth-1-ylmethyl)indol-3-yl]ethyl]amino]-9H-purin-9-yl]

Formula (IV): $R_1$=H, n=1, $R_2$=naphth-1-yl, $R_8$=

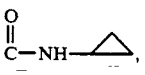

$R_9, R_{10}$=

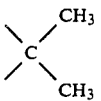

The compound of Example 60 was prepared by the procedure of Example 46 using the uronamide prepared in Example 3:

EXAMPLE 60

β-D-Ribofuranuronamido-1-[6-[[2-[1-(4-chlorobenzyl)indol-3-yl]ethyl]amino]-9H-purin-9-yl]-1-deoxy-N-(1,1-dimethyl-2-hydroxyethyl)-2,3-O-(1-methylethylidene)

Formula (IV): $R_1$=H, n=1, $R_2$=4-chlorophenyl, $R_8$=

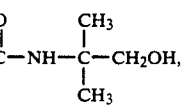

$R_9, R_{10}$=

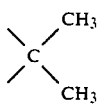

EXAMPLE 61

β-D-Ribofuranuronamido-N-cyclopropyl-1-deoxy-2,3-O-(1-(4-chlorobenzyl)indol-3-yl]ethyl]amino]-9H-purin-9-yl]-N-cyclopropyl-1-deoxy Formula (I): $R_1=H$, $n=1$, $R_2=$4-chlorophenyl, $R_3=$

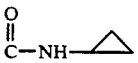

7.2 g of the purine obtained in Example 46 are placed in 135 ml of 1N HCl. The mixture is heated at 60° C. for 3 h and cooled. The solution is decanted to separate the aqueous phase from the more or less viscous gum formed. The aqueous phase is neutralized with a sodium bicarbonate solution and extracted with chloroform. The organic phases are combined with the gum obtained previously. The mixture is washed with water, dried and concentrated to give 7 g of a cream-colored solid.

The compound is purified by chromatography on silica gel (eluent: chloroform 95%/methanol 5%) to give 3.7 g of β-D-ribofuranuronamido-1-[6-[[2-[1-(4-chlorobenzyl)indol-3-yl]ethyl]amino]-9H-purin-9-yl]-N-cyclopropyl-1-deoxy.

Empirical formula: $C_{30}H_{30}ClN_{74}$.
Melting point: 225° C.

The same compound 61 can be obtained by hydrolysis in a formic acid medium (212 ml of a 50% solution) with heating at 70° C. for 75 min.

The compounds of Examples 62 to 75 were prepared according to Example 61;

EXAMPLE 62

β-D-Ribofuranuronamido-N-cyclopropyl-1-[6-[[2-[1-(4-chlorobenzyl)indol-3-yl]ethyl]amino]-9H-purin-9-yl]-1-deoxy-N-(1,1-dimethyl-2-hydroxyethyl)

Formula (I): $R_1=H$, $n=1$, $R_2=$4-chlorophenyl, $R_3=$

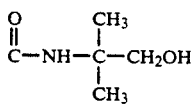

Purified by chromatography twice in succession on silica gel (eluent: chloroform 90%/methanol 10%).
Empirical formula: $C_{31}H_{34}ClN_7O_5$.
Melting point: 189° C.

EXAMPLE 63

β-D-Ribofuranuronamido-N-cyclopropyl-1-deoxy-1-deoxy-1-[6-[[2-[1-(2-methoxyethyl)indol-3-yl]ethyl]amino]-9H-purin-9-yl]

Formula (I): $R_1=H$, $n=2$, $R_2=$methoxy, $R_3=$

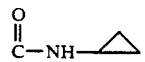

Purified by chromatography on silica gel (eluent: chloroform 95%/methanol 5%).
Empirical formula: $C_{26}H_{31}N_7O_5$.
Melting point: 132° C.

EXAMPLE 64

β-D-Ribofuranuronamido-N-cyclopropyl-1-[6-[[2-[1-cyclopentylindol-3-yl]ethyl]amino]-9H-purin-9-yl]-N-cyclopropyl-1-deoxy Formula (I): $R_1=H$, $n=0$, $R_2=$cyclopentyl, $R_3=$

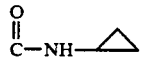

Purified by chromatography on silica gel (eluent: chloroform 95%/methanol 5%).
Empirical formula: $C_{28}H_{33}N_7O_4$.
Melting point: 141° C.

EXAMPLE 65

β-D-Ribofuranuronamido-N-cyclopropyl-1-deoxy-1-[6-[[2-[1-isopropylindol-3-yl]ethyl]amino]-9H-purin-9-yl]

Formula (I): $R_1=H$, $n=0$, $R_2=$isopropyl, $R_3=$

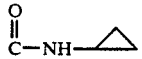

Purified by chromatography on silica gel (eluent: chloroform 90%/methanol 10%).
Empirical formula: $C_{26}H_{31}N_7O_4$.
Melting point: 135° C.

EXAMPLE 66

β-D-Ribofuranuronamido-N-cyclopropyl-1-deoxy-1-[6-[[2-[1-(4-methylbenzyl)indol-3-yl]ethyl]amino]-9H-purin-9-yl]

Formula (I): $R_1=H$, $n=1$, $R_2=$4-methylphenyl, $R_3=$

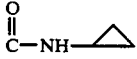

Purified by chromatography on silica gel (eluent: chloroform 905/methanol 105).
Empirical formula: $C_{31}H_{33}N_7O_4 \cdot H_2O$.
Melting point: 144° C.

EXAMPLE 67

β-D-Ribofuranuronamido-N-cyclopropyl-1-deoxy-1-[6-[[2-[1-(3,4-dimethylbenzyl)indol-3-yl]ethyl]amino]-9H-purin-9-yl]

Formula (I): $R_1=H$, $n=1$, $R_2=$3,4-dimethylphenyl, $R_3=$

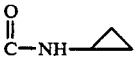

Purified by chromatography on silica gel (eluent: chloroform 95%/methanol 5%).
Empirical formula: $C_{32}H_{35}N_7O_4 \cdot H_2O$.
Melting point: 134° C.

EXAMPLE 68

β-D-Ribofuranuronamido-N-cyclopropyl-1-deoxy-1-[6-[[2-[1-(2,5-dimethylbenzyl)indol-3-yl]ethyl]amino]-9H-purin-9-yl]

Formula (I): $R_1=H$, $n=1$, $R_2=$2,5-dimethylphenyl, $R_3=$

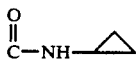

Purified by chromatography on silica gel (eluent: chloroform 955/methanol 5%).
Empirical formula: $C_{32}H_{35}N_7O_4 \cdot 0.5H_2O$.
Melting point: 130° C.

EXAMPLE 69

β-D-Ribofuranuronamido-N-cyclopropyl-1-deoxy-1-[6-[[2-[1-(2-N-morpholinoethyl)indol-3yl]ethyl]amino-9H-purin-9-yl]

Formula (I): $R_1=H$, $n=1$, $R_2=$morpholino, $R_3=$

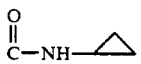

Purified by chromatography on silica gel (eluent: chloroform 95%/methanol 10%).
Empirical formula: $C_{29}H_{36}N_8O_5 \cdot 0.5H_2O$.
Melting point: 109°–110° C.

EXAMPLE 70

β-D-Ribofuranuronamido-N-cyclopropyl-1-deoxy-1-[6-[[2-[1-(2-N,N-dimethylaminoethyl)indol-3-yl]ethyl]amino]-9H-purin-9-yl]

Formula (I): $R_1=H$, $n=1$, $R_2=$N,N-dimethylamino, $R_3=$

Purified by chromatography on silica gel (eluent: chloroform 80%/isopropylamine 20%).
Empirical formula: $C_{27}H_{34}N_8O_4 \cdot 0.5H_2O$.
Melting point: 112° C.

EXAMPLE 71

β-D-Ribofuranuronamido-N-cyclopropyl-1-deoxy-1-[6-[[2-[1-(2-N-piperidinoethyl)indol-3-yl]ethyl]amino]-9H-purin-9-yl]

Formula (I): $R_1=H$, $n=1$, $R_2=$piperidino, , $R_3=$

Purified by chromatography on silica gel (eluent: chloroform 80%/methanol 20%).
Empirical formula: $C_{30}H_{38}N_8O_4$.
Melting point: 109° C.

EXAMPLE 72

β-D-Ribofuranuronamido-N-cyclopropyl-1-deoxy-1-[6-[[2-[1-(2-N-pyrrolidinoethyl)indol-3-yl]ethyl]amino]-9H-purin-9-yl]

Formula (I): $R_1=H$, $n=1$, $R_2=$pyrrolidino, $R_3=$

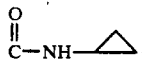

Purified by chromatography on silica gel (eluent: chloroform 80%/methanol 20%).
Empirical formula: $C_{29}H_{36}N_8O_4 \cdot 0.5H_2O$.
Melting point: 126° C.

EXAMPLE 73

β-D-Ribofuranuronamido-N-cyclopropyl-1-deoxy-1-[6-[[2-[1-(3,4-dichlorobenzyl)indol-3-yl]ethyl]amino]-9H-purin-9-yl]

Formula (I): $R_1=H$, $n=1$, $R_2=$3,4-dichlorophenyl, $R_3=$

Purified by chromatography on silica gel (eluent: chloroform 95%/methanol 5%).
Empirical formula: $C_{30}H_{29}Cl_2N_7O_4 \cdot 0.8H_2($.
Melting point: 141° C.

EXAMPLE 74

β-D-Ribofuranuronamido-N-cyclopropyl-1-deoxy-1-[6-[[2-[1-(pyrid-3-ylmethyl)indol-3-yl]ethyl]amino]-9H-purin-9-yl]

Formula (I): $R_1=H$, $n=1$, $R_2=$pyrid-3-yl, $R_3=$

Purified by recrystallization from 2-methoxyethanol.
Empirical formula: $c_{29}H_{30}N_8O_4 \cdot 0.5CH_3OCH_2CH_2OH$.
Melting point: 239° C.

EXAMPLE 75

β-D-Ribofuranuronamido-N-cyclopropyl-1-deoxy-1-[6-[[2-[1-(naphth-1-ylmethyl)indol-3-yl]ethyl]amino]-9H-purin-9-yl]

Formula (I): $R_1=H$, $n=1$, $R_2=$naphth-1-yl, $R_3=$

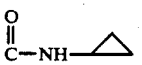

Purified by chromatography on silica gel (eluent: chloroform 95%/methanol 5%) followed by recrystallization from isopropanol.
Empirical formula: $C_{34}H_{33}N_7O_4$.
Melting point: 168° C.

EXAMPLE 76

$N^6$-[2-[1-(4Chlorobenzyl)indol-3-yl]ethyl]amino]-9H-purin-9-yl]-adenosine

Formula (IV): $R_1=H$, $n=1$, $R_2=$4-chlorophenyl, $R_8=CH_2OH$, $R_9=R_{10}=H$ 4.5 g of 1-(4-chlorobenzyl)-3-(2-aminoethyl)indole hydrochloride, prepared in Example 29 to 30, are placed in 100 ml of ethanol. 2.1 g of triethylamine and then 2 g of 6-chloroadenosine are added.

The whole is refluxed for 6 h and cooled. The precipitate obtained is filtered off and washed with ethanol and then with ether.

Recrystallization from ethanol gives 2.5 g of $N^6$-[2-[1-(4-chlorobenzyl)indol-3yl]ethyl]adenosine.

Melting point: 181° C.

The compounds of Examples 77 and 78 were prepared according to Example 76:

EXAMPLE 77

$N^6$-[2-[1-Benzylindol-3yl]ethyl]adenosine

Formula (IV): $R_1=H$, $n=1$, $R_2=$phenyl, $R_8=CH_2OH$, $R_9=R_{10}=H$

Purified by recrystallization from ethanol.
Melting point: 158° C.

EXAMPLE 78

$N^6$-[2-[1-(2,5-Dichlorobenzyl)indol-3yl]ethyl]adenosine

Formula (IV): $R_1=H$, $n=1$, $R_2=$2,6-dichlorophenyl, $R_8=CH_2OH$, $R_9=R_{10}=H$ Purified by recrystallization from ethanol.
Melting point: 192° C.

The alcohols of Examples 76, 77 and 78 may be oxidized to the acid by reaction with an oxidizing agent such as chromium trioxide in acetone in the presence of sulfuric acid, or potassium permanganate in water in the presence of ammonia. They will subsequently give the corresponding acid chlorides after reaction with thionyl chloride and then the ribofuranuronamide derivatives of the same type as those of Examples 61, 62, 73 or 75 by reaction with appropriate amines.

PHARMACOLOGY

The pharmacological activity of the products of the Examples was evaluated by two different approaches: binding to adenosine receptors and/or demonstration of analgesic activity by the phenylbenzoquinone test.

I PROCEDURE

1. Binding to Adenosine Receptors

Principle

The affinity of the products of the Examples for the rat central $A_1$ and $A_2$ adenosinergic receptors is determined by the competitive technique using a radioactive ligand specifically bound either to the $A_1$ receptors ([$^3$H] PIA) or to the $A_2$ receptors ([$^3$H] NECA).

Method

Method of Studying the $A_1$ Receptors

Membrane preparation

After the animal has been sacrificed by decapitation, the brain is quickly removed and washed in cold isotonic solution. The two hemispheres are separated and weighed and each of them is introduced into a polyallomer tube containing 25 volumes of cold homogenization buffer. Homogenization is effected using an Ultra-Turrax for 30 seconds (3 times 10 seconds with 10-second intervals, 70% of the maximum speed). The ground material obtained is centrifuged at 1000 g (~3000 rpm) for 10 minutes at 4° C.

The supernatant is centrifuged again at 48,000 g (~20,000 rpm) for 20 minutes at 4° C.

When this step is complete, the residue is taken up with 4 volumes of homogenization buffer, resuspended using a Vortex and homogenized with the Ultra-Turrax. Adenosine deaminase is then added at a rate of 1 U/ml, i.e. 1 µl/ml of homogenate, using a 10 µl Hamilton syringe.

After this treatment, the homogenate is shaken for 30 minutes at room temperature and then centrifuged at 80,000 g (~20,000 rpm) for 30 minutes at 4° C.

The residue obtained is resuspended in 10 volumes of homogenization buffer and passed through the Ultra-Turrax for 20 seconds (2 times 10 seconds with a 10-second interval, 70% of the maximum speed).

The homogenate prepared in this way is used for the competitive tests. It is kept at 4° C. if the studies take place the same day, or stored at $-20°$ C. in the form of 10 ml aliquots.

Competitive Test after the homogenate has been thawed at room temperature, it is passed through a Potter mill (6 manual to-and-fro movements, speed 5), diluted to 2/5 in incubation buffer and placed in a water bath thermostated at 4° C., with shaking, until the end of the experiment.

50 µl of [$^3$H] PIA at 100 nM, i.e. 2.5 nM in the final reaction medium allowing for the 1/40 dilution, and 50 µl of the product of the Example at the concentrations considered ($10^{-5}$ M and $10^{-7}$ M) are introduced into the reaction tubes. The reaction is initiated by the addition of 1 ml of homogenate and 900 µl of incubation buffer. The procedure is identical for all the beta-blockers studied.

The tubes are shaken and incubated in a water bath at 20° C. for 30 minutes. When the incubation is complete, the contents of the tubes are filtered on Whatman GF/B paper. Each tube is washed twice with 2 ml of rinsing buffer and then the filters themselves are rinsed with 3 ml of this same buffer.

The filters are then transferred to counting flasks and 10 ml of liquid scintillator (Ready Solv HP/b, Beckman) are added.

After they have been shaken, the flasks are stored in a refrigerator overnight and the radioactivity is then determined in a liquid scintillation counter.

3 tests are performed for each concentration studied. The non-specific binding of the [$^3$H] PIA is assessed by measuring the amount of radioactivity retained on the filter in the presence of $10^{-5}$ M phenylisopropyladenosine (PIA). The value of the non-specific binding is systematically subtracted from that of the tests.

Method of Studying the $A_2$ Receptors

Membrane Preparation

After decapitation of the animal, the brain is quickly removed and washed in cold isotonic solution. The two hemispheres are separated and the striatum is removed from each of them (Bruns et al., 1986), weighed and introduced into a polyallomer tube containing 10 volumes of cold homogenization buffer. The tissue is homogenized with an Ultra-Turrax for 30 seconds (3 times 10 seconds with 10-second intervals, 70% of the maximum speed). The ground material is centrifuged at 50,000 g (~20,500 rpm) for 10 minutes at 4° C.

The residue obtained is resuspended in 10 volumes of homogenization buffer using a Vortex and homogenized with the Ultra-Turrax (5 to 10 seconds, 70% of the maximum speed).

Adenosine deaminase is then added at a rate of 1 U/ml, i.e. 1 μl/ml of homogenate, using a 10 μl Hamilton syringe. The homogenate treated in this way is shaken at room temperature for 30 minutes.

When the incubation is complete, the homogenate is centrifuged at 50,000 g (~20,500 rpm) for 10 minutes at 4° C.

The residue is taken up with 5 volumes of cold homogenization buffer and passed through the Ultra-Turrax (2 times 10 seconds with a 10-second interval, 70% of the maximum speed) and the homogenate prepared in this way is finally frozen at −70° C.

Competitive Test

After the homogenate has been thawed at room temperature, 15 volumes of incubation buffer are added. The homogenate is shaken on a Vortex, passed through a Potter mill (6 to-and-fro movements, speed 6), diluted to 1/10 in incubation buffer and finally placed in a water bath thermostated at 4° C., with shaking, until the end of the experiment.

50 μl of [$^3$H] NECA at 160 nM, i.e. 4 nM in the final reaction medium allowing for the 1/40 dilution, and 50 μl of the product of the Example at the concentrations considered ($10^{-5}$ M and $10^{-7}$ M) are introduced into the reaction tubes. The reaction is initiated by the addition of 1 ml of homogenate and 900 μl of incubation buffer. The procedure is similar for all the compounds studied.

The tubes are shaken and incubated in a water bath at 25° C. for 60 minutes. When the incubation is complete, the contents of the tubes are filtered on Whatman GF/B paper. Each tube is washed twice with 2 ml of rinsing buffer and then the filters themselves are rinsed with 3 ml of this same buffer before being transferred to counting flasks.

10 ml of liquid scintillator (Ready Solv HP/b, Beckman) are added to all the flasks. These are shaken and stored in a refrigerator overnight. The radioactivity is determined in a liquid scintillation counter.

3 tests are performed for each concentration studied. The non-specific binding of the [$^3$H] NECA is determined by measuring the amount of radioactivity retained on the filter in the presence of 5 μm N-ethylcarboxamidoadenosine (NECA). The value of the non-specific binding is systematically subtracted from that of the tests.

Treatment of the Data

The results are expressed for each product in the form of the percentage displacement (n=3) of the labeled radioligand at concentrations of $10^{-5}$ M and $10^{-7}$ M.

2. Phenylbenzoquinone Test

Method

The intraperitoneal injection of phenylbenzoquinone causes twisting and stretching movements in mice. Analgesics prevent or reduce this syndrome, which can be considered as the exteriorization of diffuse abdominal pain.

A 0.02% solution of phenylbenzoquinone in water is administered in a volume of 1 ml/100 g.

The products of the examples are administered orally one hour before the injection of phenylbenzoquinone.

The stretching and twisting movements are counted for each mouse over an observation period of 5 minutes.

II RESULTS

The results of the experiments demonstrate the affinity of the products of the Examples for adenosine receptors and their analgesic properties are presented in Tables 1 and 2 respectively.

TABLE 1

| | % displacement of the labeled ligand | | | |
|---|---|---|---|---|
| | A1 | | A2 | |
| Product of | 1E-5M | 1E-7M | 1E-5M | 1E-7M |
| Example 61 | 98 | 47 | 91 | 30 |
| Example 63 | — | — | 90 | 19 |
| Example 64 | 96 | 21 | 90 | 28 |
| Example 65 | 87 | 4 | — | — |
| Example 66 | 97 | 37 | 89 | 21 |
| Example 67 | 96 | 29 | 83 | 13 |
| Example 68 | 93 | 26 | 84 | 9 |
| Example 69 | 93 | 68 | 90 | 12 |
| Example 70 | 100 | 91 | 94 | 44 |
| Example 71 | 99 | 94 | 91 | 46 |
| Example 76 | 100 | 71 | 97 | 59 |
| Example 77 | 100 | 67 | 95 | 30 |

TABLE 2

| | Phenylbenzoquinone test 50% inhibitory dose |
|---|---|
| Product of | mg/kg p.o. |
| Example 61 | 0.90 |
| Example 63 | 10 |
| Example 64 | 0.3 |
| Example 65 | 0.3 |
| Example 66 | 3 |
| Example 67 | 3 |
| Example 68 | 2.4 |
| Example 76 | 41 |
| Example 77 | ≈100 |

III TOXICOLOGY

The tolerance of the products of the Examples was assessed in rats after oral administration. It was found to be good up to a dose of 100 ml/kg.

IV CONCLUSION

The products of the Examples described in the present invention possess particularly valuable analgesic properties, whose original mechanism of action results from an interaction with adenosine receptors.

What is claimed is:

1. An adenosine compound of the formula

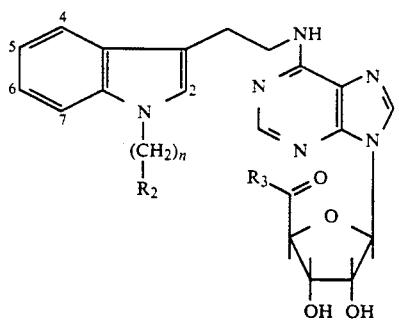

and pharmaceutically acceptable addition salts thereof, in which:

n is an integer equal to 0, 1 or 2;

$R_2$ is an alkyl radical having 1 to 6 carbon atoms, a cycloalkyl radical having 3 to 7 carbon atoms, an alkoxy radical having 1 to 6 carbon atoms, a phenyl radical which is unsubstituted, monosubstituted or polysubstituted by a halogen atom, an alkyl radical having 1 to 6 carbon atoms, or an alkoxy racial having 1 to 6 carbon atoms, a naphthyl radical, a pyridyl radical, or when n is equal to 2, a group —N $R_5R_6$ in which $R_5$ and $R_6$ are both an alkyl radical having 1 to 6 carbon atoms or form together with the nitrogen atom to which they are attached, a heterocycle selected from the group consisting of pyrrolidine, piperidine, piperazine and morpholine; and $R_3$ is a group —$NHR_7$ in which $R_7$ is a hydrogen atom, an alkyl radical having 1 to 6 carbon atoms, a cycloalkyl radical having 3 to 7 carbon atoms, or an alkyl radical having 1 to 6 carbon atoms of which one of the hydrogen atoms is substituted by one hydroxyl group.

2. A compound according to claim 1, which is selected from the group consisting of

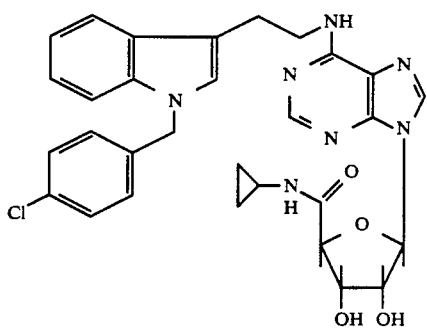

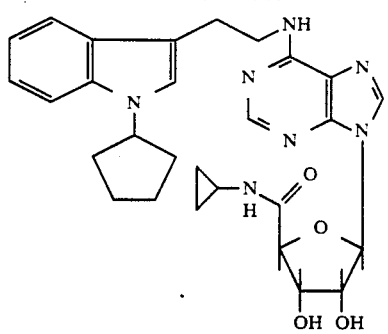

-continued

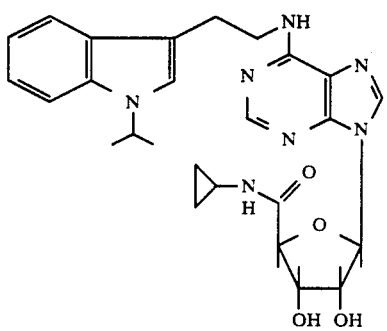

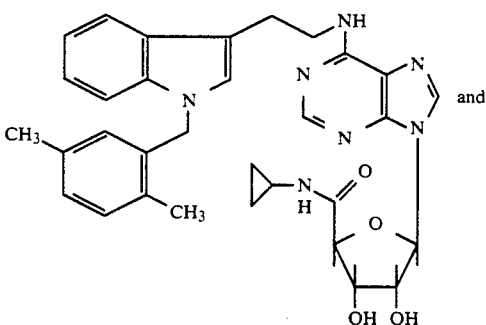

and

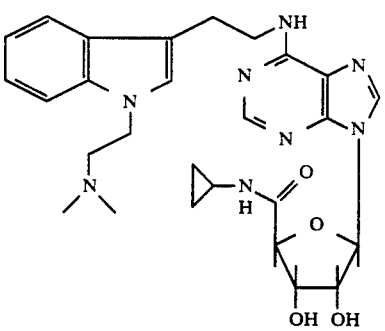

3. A compound according to claim 1 wherein $R_2$ is a radical selected from the group consisting of para-chlorophenyl, cyclopentane, isopropyl, 2,5-dimethylphenyl and piperidine.

4. A compound according to claim 1 wherein $R_3$ is an N-cyclopropylamine radical.

5. A pharmaceutical composition which comprises a pharmaceutically effective amount of a compound as defined in claim 1, or one of its pharmaceutically acceptable addition salts, incorporated in a pharmaceutically acceptable excipient, vehicle or carrier.

* * * * *